(12) United States Patent
Larsson

(10) Patent No.: US 10,598,631 B2
(45) Date of Patent: Mar. 24, 2020

(54) ELECTROPHORESIS SEPARATION METHOD

(71) Applicant: GE Healthcare Bio-Sciences AB, Uppsala (SE)

(72) Inventor: Kjell Larsson, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 127 days.

(21) Appl. No.: 15/129,335

(22) PCT Filed: Mar. 23, 2015

(86) PCT No.: PCT/EP2015/056056
§ 371 (c)(1),
(2) Date: Sep. 26, 2016

(87) PCT Pub. No.: WO2015/144618
PCT Pub. Date: Oct. 1, 2015

(65) Prior Publication Data
US 2017/0102360 A1    Apr. 13, 2017

(30) Foreign Application Priority Data
Mar. 28, 2014    (SE) ..................................... 1450365

(51) Int. Cl.
*G01N 27/447*    (2006.01)
*B03C 5/00*    (2006.01)

(52) U.S. Cl.
CPC ......... *G01N 27/44743* (2013.01); *B03C 5/00* (2013.01); *G01N 27/44782* (2013.01); *G01N 27/44795* (2013.01)

(58) Field of Classification Search
CPC ....... G01N 27/44743; G01N 27/44782; G01N 27/44795
See application file for complete search history.

(56) References Cited

U.S. PATENT DOCUMENTS 5,275,710 A    1/1994 Gombocz et al.
5,405,516 A    4/1995 Bellon
(Continued)

FOREIGN PATENT DOCUMENTS

DE    19700626 A1    7/1998
DE    202013102432 U1    7/2013
(Continued)

OTHER PUBLICATIONS

International Search Report and Written Opinion regarding International Application No. PCT/EP2015/056056, dated Jul. 29, 2015, 16 pages.
(Continued)

*Primary Examiner* — Susan D Leong
(74) *Attorney, Agent, or Firm* — Eversheds Sutherland (US) LLP

(57) ABSTRACT

Method for electrophoretic separation using a separation gel arrangement with a gel member and one or more sample wells for receiving sample liquid to be separated, the sample wells being in fluidic contact with the gel member, the method comprising the steps: adding a sample liquid to be separated in one or more of the sample wells, applying an electric field over the gel member to drive an electrophoretic separation process, whereby sample constituents are drawn from the sample liquid in the sample well(s) into the gel member for separation, and when a removal criteria is met: discontinuing loading of sample constituents into the separation gel.

17 Claims, 15 Drawing Sheets

(56) References Cited

U.S. PATENT DOCUMENTS

| | | | |
|---|---|---|---|
| 5,464,515 A | 11/1995 | Bellon | |
| 6,024,854 A | 2/2000 | Gilchrist | |
| 6,319,379 B1* | 11/2001 | Davidson | G01N 27/44743 |
| | | | 204/451 |
| 6,406,602 B1 | 6/2002 | Cahill et al. | |
| 6,428,668 B1 | 8/2002 | Ansorge et al. | |
| 6,485,690 B1* | 11/2002 | Pfost | B01J 19/0046 |
| | | | 422/552 |
| 7,102,005 B2 | 9/2006 | Agnew et al. | |
| 2001/0050699 A1 | 12/2001 | Hickman | |
| 2003/0032201 A1* | 2/2003 | Flesher | G01N 27/44704 |
| | | | 436/517 |
| 2004/0038306 A1* | 2/2004 | Agnew | G01N 33/50 |
| | | | 435/7.1 |
| 2004/0106153 A1* | 6/2004 | Dratz | G01N 33/533 |
| | | | 435/7.1 |
| 2005/0029104 A1 | 2/2005 | Kobos et al. | |
| 2006/0191793 A1 | 8/2006 | Yamamoto | |
| 2009/0238723 A1* | 9/2009 | Guharay | G01N 21/658 |
| | | | 422/68.1 |
| 2011/0042213 A1 | 2/2011 | Updyke et al. | |

FOREIGN PATENT DOCUMENTS

| | | |
|---|---|---|
| EP | 0476890 A2 | 3/1992 |
| EP | 0735365 A2 | 10/1996 |
| EP | 1132734 A1 | 9/2001 |
| WO | 9013813 A1 | 11/1990 |
| WO | 02/064253 A2 | 8/2002 |
| WO | 2011028535 A2 | 3/2011 |
| WO | 2013/180642 A1 | 12/2013 |
| WO | 2014007720 A1 | 1/2014 |

OTHER PUBLICATIONS

International-Type Search Report regarding SE Application No. 1450365-0, dated Nov. 7, 2014, 13 pages.

Chinese Office Action for CN Application No. 201580027783.5 dated Aug. 2, 2018 (21 pages with English translation).

Japanese Office Action for JP Application No. 2017-501485 dated Aug. 23, 2019 (6 pages, with English translation).

* cited by examiner

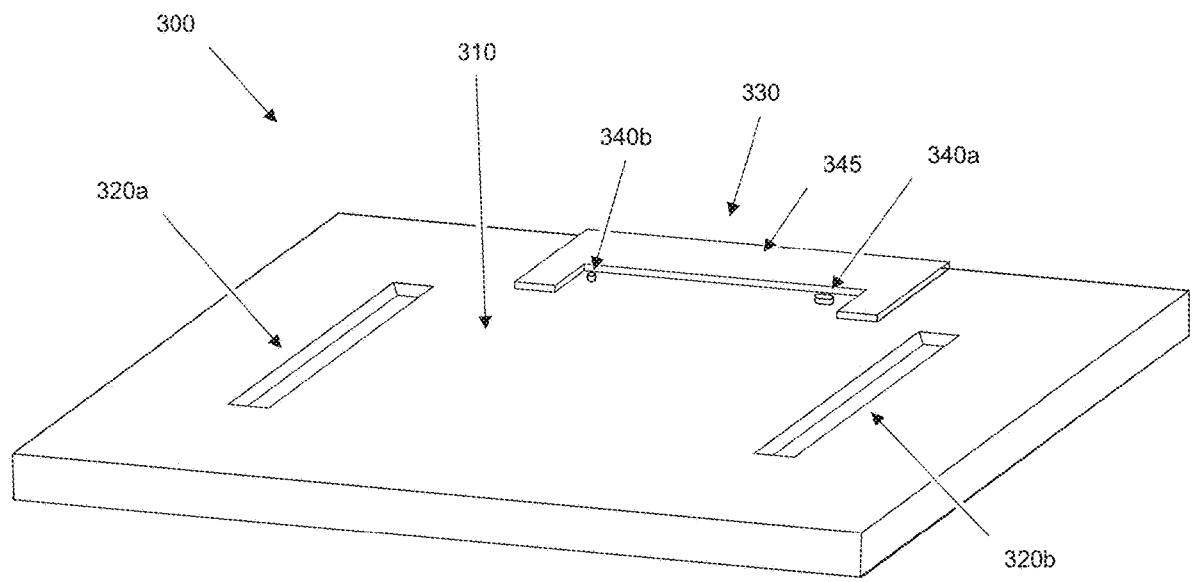
Fig 4
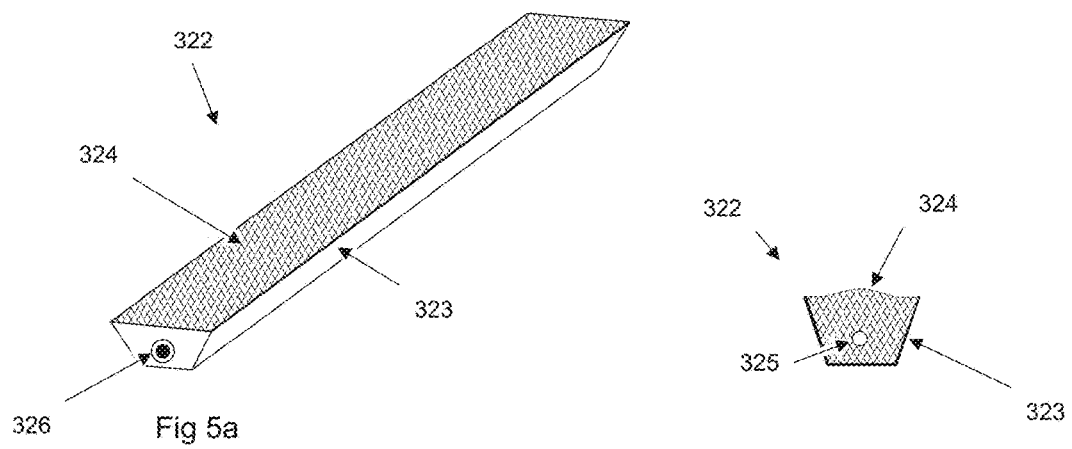
Fig 5a
Fig 5b

Different samples at high concentration without and with the clean up procedure

ELECTROPHORESIS SEPARATION METHOD

CROSS-REFERENCE TO RELATED APPLICATIONS

This application is a filing under 35 U.S.C. 371 of international application number PCT/EP2015/056056, filed Mar. 23, 2015, which claims priority to SE application number 1450365-0, filed Mar. 28, 2014, the entire disclosures of each of which are hereby incorporated by reference.

FIELD OF THE INVENTION

The present invention relates to an and a well clean-up device, and more particularly to an electrophoresis separation method and well clean-up unit with improved handling.

BACKGROUND OF THE INVENTION

Electrophoresis is a commonly used method for analysis, wherein charged molecules and particles migrate in a separation medium, usually a gel, which is subjected to an electrical field between two electrodes. Separation of proteins may be by isoelectric point (pI), molecular weight, electric charge, or a combination of these factors.

The separation gel is usually placed on a support and two opposing ends of the gel are contacted with an electrode buffer in solution or rigid form. The electrodes may be inserted in vessels containing the electrode buffers. The buffer solutions form both the electrolytic medium and a reservoir for ions to keep the pH and other parameters constant. After separation, the molecules are detected and identified in different manners: e.g. visually by staining the gel or by optical means such as scanning or imaging the stained gel or labeller samples by a laser scanner or the like.

Gel electrophoresis is today routinely used for separating biomolecules such as proteins, peptides, nucleic acids etc. Samples are handled in different types of screening, identifying (cell signaling, expression & purification) or in clinical tests. Protein samples can derivate from e.g. human, mammalian tissue, cell lysates or bacterial, insect or yeast cellular systems. The electrophoretic conditions for different types of molecules are different and have to be adapted in many cases. Thus, both the gel and the buffer solutions must often be chosen for each type of sample.

Labeling proteins with fluorescent dyes has become the method of choice for tracking and quantifying proteins. Fluorescent labeling results in good sensitivity and a broad linear detection range. It also presents a convenient alternative to protein staining methods and is a safer option to radioactive labeling.

The choice of dye and labeling conditions depend on the application. For immunological applications, e.g. antibody labeling, it is important to get high signal intensity and the dye-to-protein ratio is optimized accordingly. For electrophoresis it is also necessary to use a suitable dye-to-protein ratio, in this case to get both high signal intensity and sharp electrophoresis bands. Furthermore, for isoelectric focusing (IEF) electrophoresis it is necessary to use charge-matched dyes to not change the isoelectric point of the protein. Pre-labeling for electrophoresis is well known (see e.g. "Electrophoresis" by Anthony T. Andrews, Clarendon Press, Oxford, 1986).

SUMMARY OF THE INVENTION

The object of the invention is to provide a new method for electrophoretic separation, an automated electrophoresis system and a sample liquid removal device, which method, system and device overcomes one or more drawbacks of the prior art. This is achieved by the electrophoresis gel unit as defined in the independent claim.

One advantage with the present invention is that it provides for improved quality of electrophoresis separation results.

A more complete understanding of the present invention, as well as further features and advantages thereof, will be obtained by reference to the following detailed description and drawings.

BRIEF DESCRIPTION OF THE DRAWINGS

FIG. 4 shows a schematic view of an electrophoresis tray that is compatible with the electrophoresis cassette for running electrophoresis experiments using the same.

FIG. 5 shows a schematic view of a buffer pad for use with an electrophoresis tray of FIG. 4.

DETAILED DESCRIPTION OF THE INVENTION

Throughout this disclosure, the separation-zone of an electrophoresis gel is defined as the part of the gel wherein the separated species of the sample are located after a completed electrophoresis run.

Figure 1:
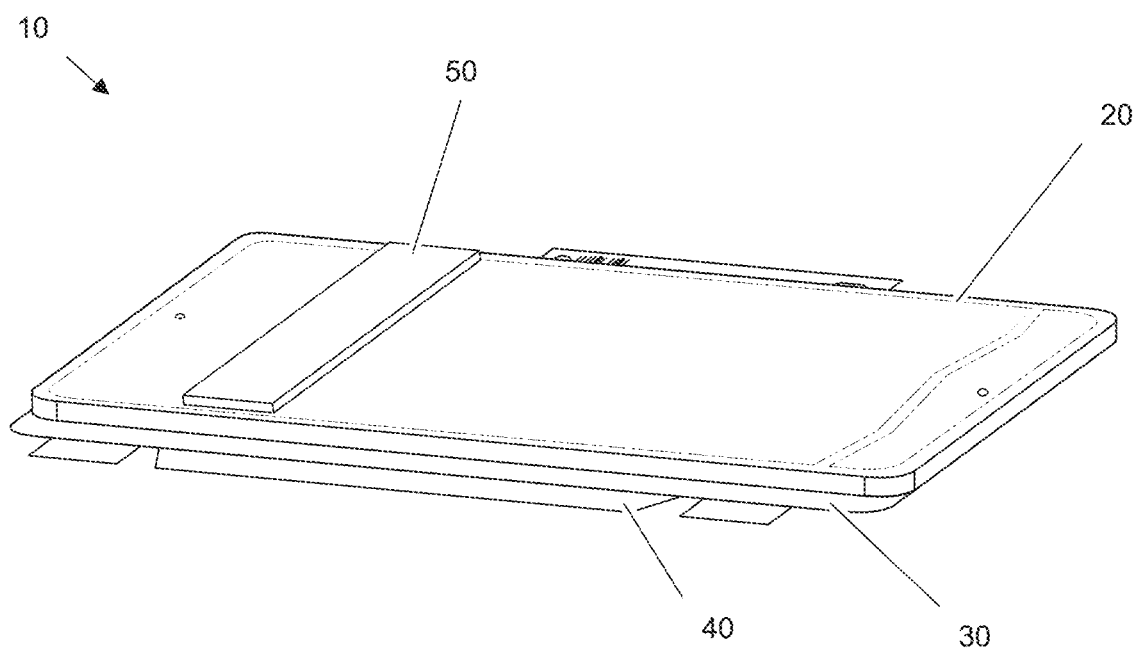
FIG. 1 is a schematic perspective view of an electrophoresis cassette according to one embodiment.

FIG. 1 is a perspective view of an electrophoresis cassette 10 disclosed in detail in WO2014/007720 which is incorporated herein in its entirety by reference. The present invention is disclosed below with reference to the cassette 10 and associated features, however it should be understood that the present invention may be involve use of other electrophoresis cassettes or devices. The cassette 10 comprises a cassette housing 20, a detachable gel support frame 30, a section-wise removable backing film 40 and a removable sample well cover 50. FIG. 1 shows the electrophoresis cassette in assembled state. The gel cassette 10 defines therein a gel compartment for molding a flat gel member 36 for electrophoretic separation.

Figure 2A:
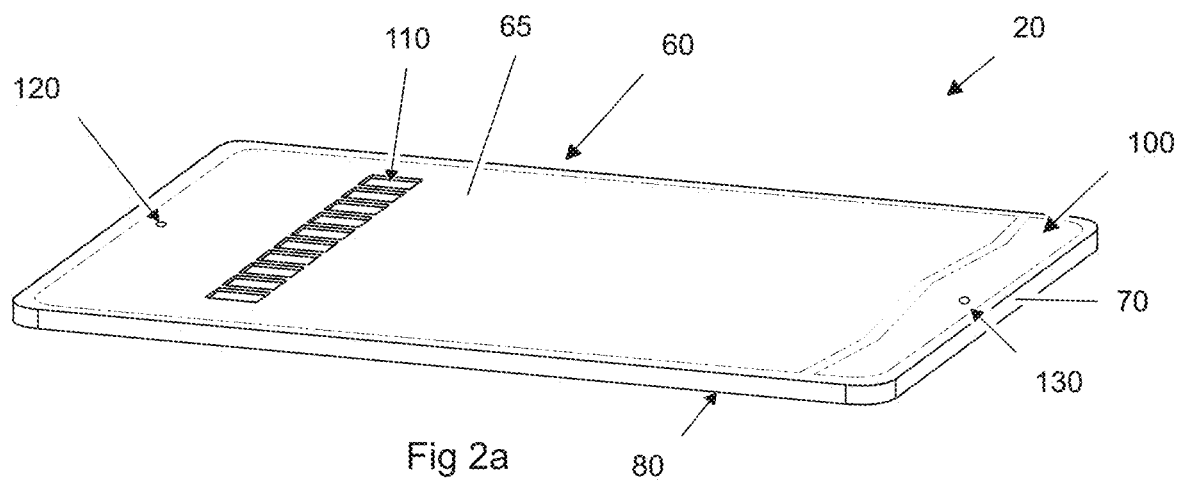
FIGS. 2a to 2f show components of the electrophoresis cassette of FIG. 1.
Figure 2B:
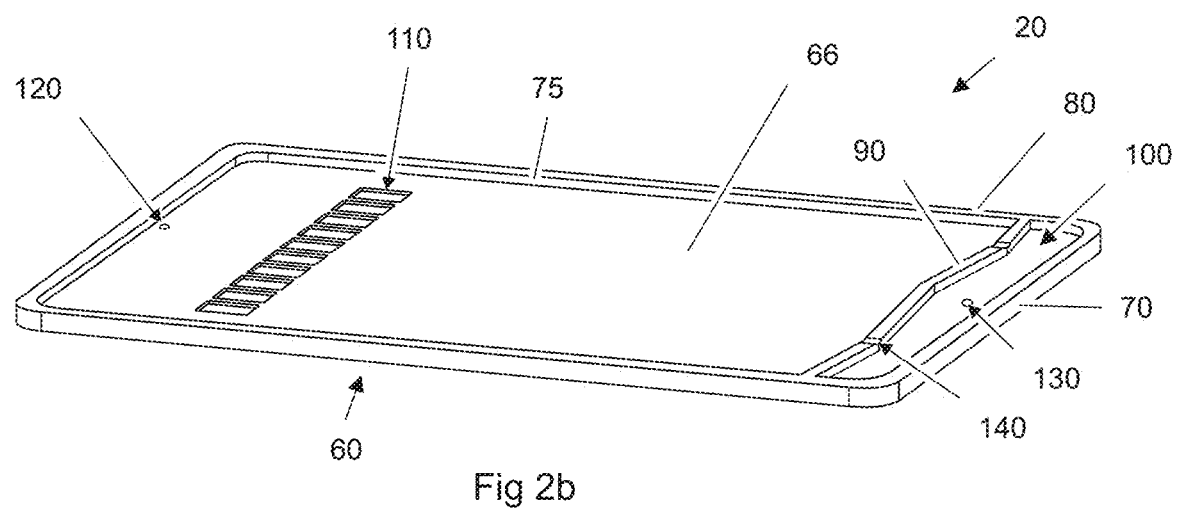

FIGS. 2a and 2b shows the cassette housing 20 with the other components of the cassette removed. FIG. 2a is a top view whereas FIG. 2b shows the cassette housing 20 from below. The cassette housing 20 is generally comprised of a thin upper wall 60 with an upper face 65 and a lower face 66, and a rim 70 that projects downwards from the upper wall 60 around its periphery with a bottom face 80 and an inner wall 75. The lower face 66 of the upper wall 60 and the inner wall 75 of the rim 70 essentially defines the gel compartment, which may be closed from below by attaching the support frame 30 and the removable backing film 40 to the lower face 80 of the rim 70, as is shown in FIG. 1 and will be discussed in more detail below. In the disclosed embodiment, the thickness of a gel member 36 molded in the cassette 10 will be essentially the same as the height of the inner wall 75 of the rim. In the disclosed embodiment, the upper wall 60 is of uniform thickness whereby the gel member 36 also will be of uniform thickness, provided that the support frame 30 and the removable backing film 40 are flat as in the disclosed embodiment. The thickness of the gel is preferably adapted to the specific gel type and the buffer system used, as well on the desired currents involved in the electrophoresis step.

Figures 2C, 2D:
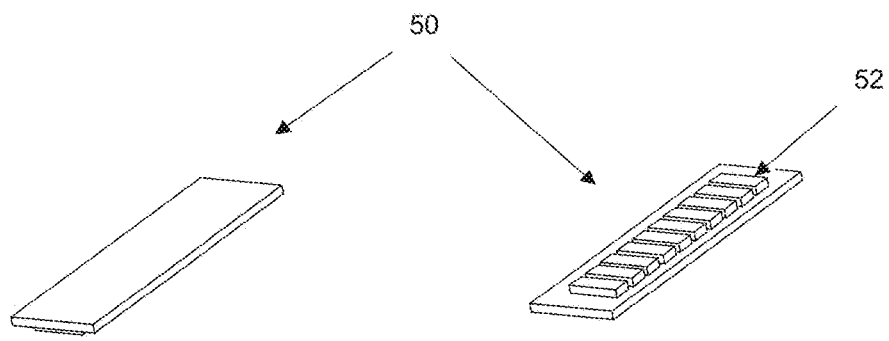

The disclosed cassette 10 is provided with 10 sample well openings 110 for enabling loading of sample onto the gel member 36 for separation, each sample well opening 110 corresponding to one electrophoresis lane during separation. The number and shape of sample well openings 110 may vary depending on the actual dimensions of the electrophoresis cassette, the type of separation and the electrophoresis gel type etc. There may be any suitable number of sample well openings 110 between 1 and e.g. 100. In FIG. 1 the sample well openings 110 are covered by a removable sample well cover 50 which is disclosed in more detail in FIGS. 2c and 2d. The sample well cover 50 is arranged to fit over the well openings 110 and to keep them closed during the molding process and storage. Before sample is to be loaded into the sample wells 110, the well cover 50 is removed to open the sample wells 110. In the disclosed embodiment, the well cover 50 comprises well forming protrusions 52 that are formed to fit in a mating relationship in the sample well openings 110 to essentially provide a sealing interaction therewith to avoid leakage of gel solution during molding and air into the cassette during storage. According to one embodiment, the well forming protrusions 52 are designed to extend below the lower face 66 of the upper wall 60 into the gel member 36 to form sample wells extending into the gel member 36 when removed. In another embodiment, the well forming protrusions 52 are designed such that they are flush with the lower face 66 of the upper wall 60 to provide an essentially flat surface of the gel member 36 and wherein sample wells are formed by the sample well openings 110. In one embodiment, the sample well cover 50 is arranged to seal against the upper face 65 of the upper wall 60 or a combination thereof.

Figure 2E:
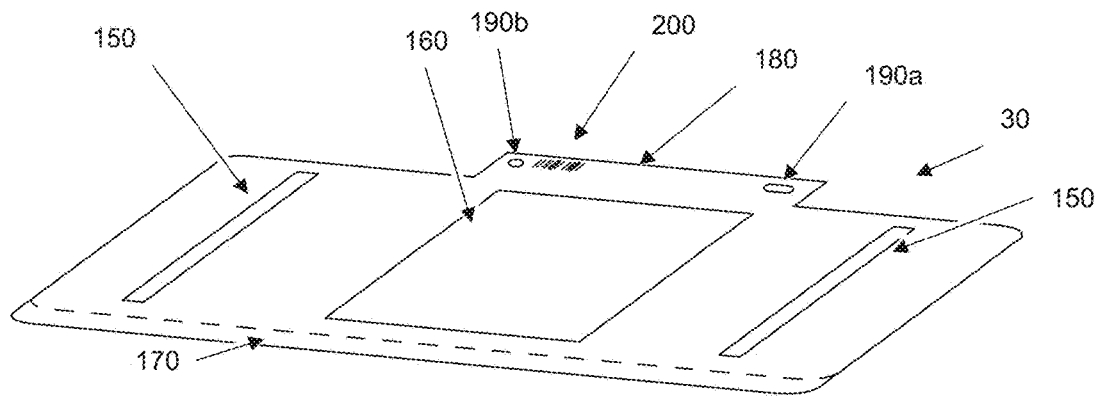
Figure 2F:
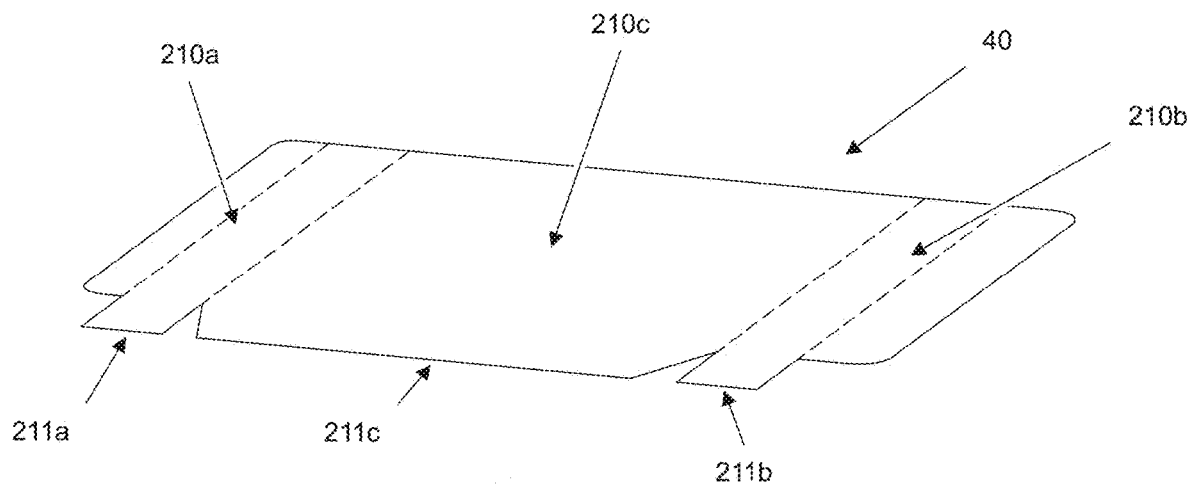

According to the disclosed embodiment, the detachable gel support frame 30 is detachably attached to the bottom face 80 of the rim 70 and the section-wise removable backing film 40 is in turn attached/laminated to the bottom of the gel support frame 30. The gel support frame 30 and the backing film 40 together provide a lower wall that closes the electrophoresis compartment and the over-fill chamber 100 for molding and storage. As is shown in FIG. 2e, the disclosed embodiment of the gel support frame 30 comprises two buffer buffer-slits 150a and 150b and a separation zone window 160 each covered from below by a respective removable section 210a-c of the backing film 40, shown in FIG. 2f. By selecting suitable material combinations and adhesive technology, the backing film may 40 be laminated onto the bottom face of the gel support frame 30 such that the respective sections 210a-c can be removed e.g. by an operator grabbing and pulling a respective peel tab 211a-c. As will be discussed in more detail below, in order to run an electrophoresis experiment, the sections 210a and 210b of the backing film 40 are removed in order to place the gel in contact with buffer pads in an electrophoresis apparatus. Following the electrophoresis run, and in order to provide access to the separation-zone of the gel member 36 for transfer/blotting and probing, the section 210b is removed to uncover the gel through the separation-zone window 160.

In order to greatly improve handling of the gel member 36 in the steps following the electrophoresis run, the gel support frame 30 is designed to stay attached to the gel member 36 after removal from the cassette 10. The support frame 30 is formed of a suitably rigid material to preserve the shape of the gel and to facilitate handling of the gel member 36 by providing accessible gripping portions that are not covered by the gel member. After removal of the section 210c of the backing film 40 the lower face of the separation zone of the gel member 36 is accessible through the separation-zone window 160.

The support frame 30 further comprises an alignment tag 180 with a predefined alignment structure defining a positional reference for alignment of the support frame 30. In the disclosed embodiment, the alignment structure in the form of two alignment holes 190a and 190b, arranged to ensure that the cassette 10 and/or the support frame 30 is properly aligned with respect to a complementary alignment structure e.g. comprising 2 pins, in an electrophoresis apparatus or the like. Further, the support frame 30 is suitably provided with an identification code 200 or the like which will make it possible to read the identity of the gel member 36 also after it has been removed from the cassette 10 in a secure way. The identification code 200 may e.g. be a machine readable code as a bar-code, matrix-code or the like, and provide the user and/or instruments with relevant information.

Figure 3:
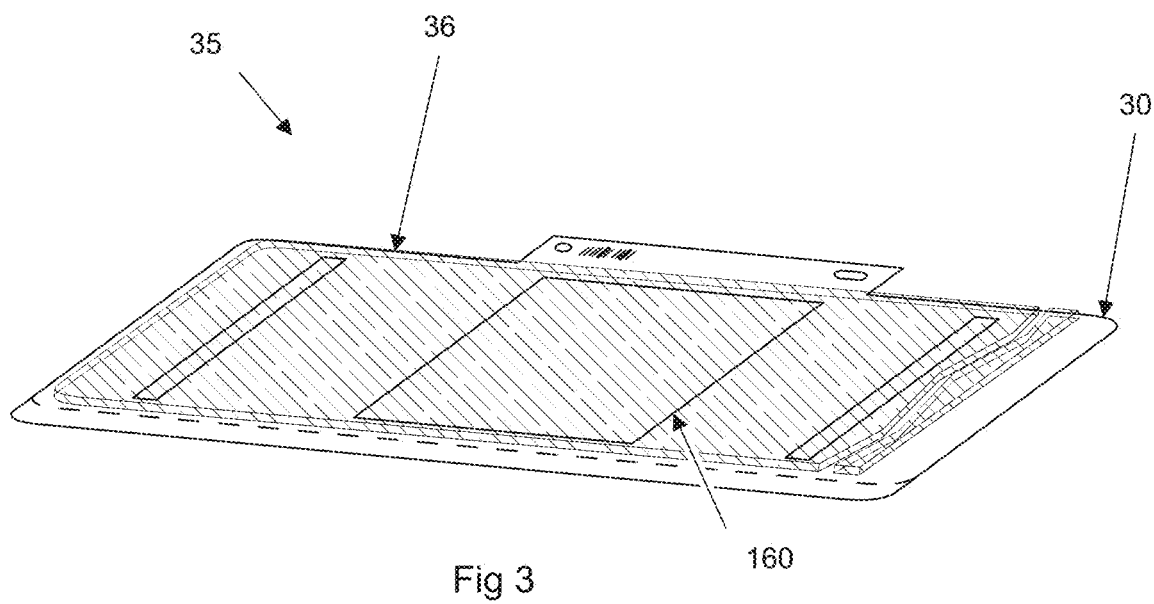
FIG. 3 shows an electrophoresis gel unit with a gel member attached to the top face of a support frame.

FIG. 3 shows an electrophoresis gel unit 35 e.g. formed by the support frame 30 with the gel member 36 attached to the top face thereof detached from the cassette housing 20. The thus formed gel member 36 is an essentially flat member with an upper and a lower face and a sample separation zone as previously defined. The support frame 30 is arranged to preserve the shape of and to facilitate handling of the gel member 36, while at the same time being formed to allow access to a section of both the upper and lower face of the gel member essentially corresponding to the separation zone. As will be shown below, the accessible section of the section gel member 36 at either face may be larger than the separation zone, but in order to allow proper transfer of separated sample from the gel member 36 to e.g. a blot membrane by immunoblotting, the accessible section at either face should not be smaller.

FIG. 4 shows a schematic view of an electrophoresis tray 300 that is compatible with the electrophoresis cassette 10 for running electrophoresis experiments using the same. In FIG. 4 the tray 300 is disclosed as a separate feature, but it may conveniently be an integral part of an electrophoresis apparatus, and it may be comprised of several components and or comprise two or more cassette positions for running two or more electrophoresis experiments in parallel. The tray 300 comprises a cassette support surface 310 for supporting at least the separation zone of an electrophoresis cassette 10 during electrophoresis. The cassette support surface 310 is flanked by a pair of buffer pad holders 320a and 320b respectively, each one arranged to hold a buffer pad 322 in a mating position with respect to the buffer connection sections at the back face of the electrophoresis cassette 10. According to one embodiment, the tray 300 comprises a heat transfer unit (not shown) connected to the cassette support surface 310 to control the temperature the electrophoresis cassette 10 during electrophoresis by heat transfer contact with a section of the back surface of the electrophoresis cassette 10. In the disclosed embodiment, the tray 300 comprises a flat top surface with two buffer pad holders 320a and 320b formed as two separate recesses therein, and an alignment structure 330 that is formed to be complementary to the alignment tag 180 of the support frame 30 to ensure proper orientation of the cassette 10 on the tray. In the disclose embodiment, the alignment structure 330 is comprised of an elongated pin 340a, a circular pin 340b and an optional wall member 345. By making the pins 340a and 340b of different cross-sectional shape, the alignment structure is made asymmetric, whereby proper orientation of the alignment tag 180 and the cassette 10 is ensured. When the cassette 10 is properly positioned on the tray 300, the buffer slits 150a and 150b of the support frame 30 are positioned at the respective buffer compartments 320a and 320b to enable mating contact between the gel exposed through the buffer slits 150a and 150b (with the respective removable section 210a and 210b of the backing film 40 removed) and a buffer pad 322, schematically shown in FIGS. 5a and 5b, placed in the respective buffer pad holders 320a and 320b, as is schematically shown in FIGS. 8a, 8b and 8c.

According to one embodiment, the buffer pad 322, schematically disclosed in FIGS. 5a and 5b comprises a cup 323 housing a buffer strip 324 and an electrode arrangement 325. FIG. 5b shows a cross sectional view of FIG. 5a. The cup further comprises an external electrical connector 326 for connecting the electrode arrangement 325 to a power source of the electrophoresis apparatus. Consequently, the tray 300 is provided with complementary electrical connectors (not shown). The cup 323 is formed to fit into the buffer pad holders 320a and 320b so that the top portion of the buffer strip 324 can be placed in contact with the gel in a cassette placed on the tray 300. The buffer strip 324 may be comprised of a buffer substance incorporated in a gel material e.g. the type disclosed in WO 87/04948. By placing the buffer strip 324 in a cup 323, changing the buffer media between electrophoresis runs is greatly facilitated, e.g. compared to placing gel strips directly in the buffer recess. As is disclosed in FIG. 5b, the gel strip 324 may be formed with a raised section to facilitate contact to the gel in the cassette 10.

Figure 6A:
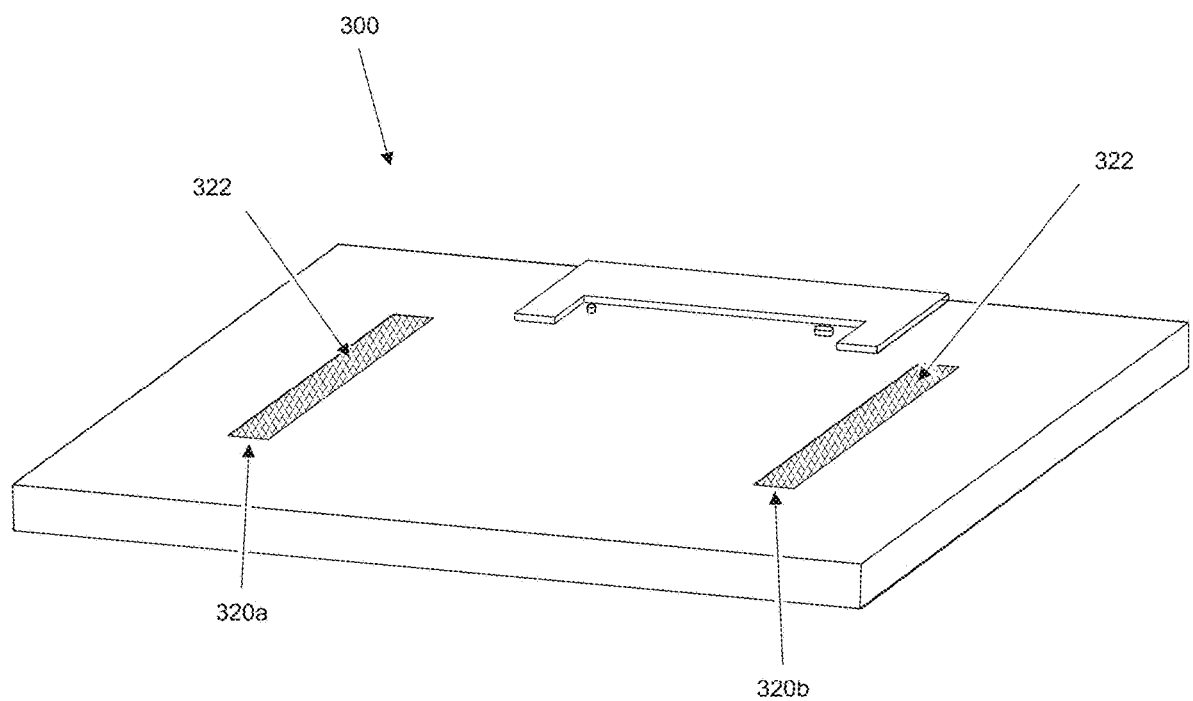
FIGS. 6 to 9 schematically show the steps involved performing an electrophoresis separation experiment using an electrophoresis cassette and a compatible electrophoresis apparatus.
Figure 6B:
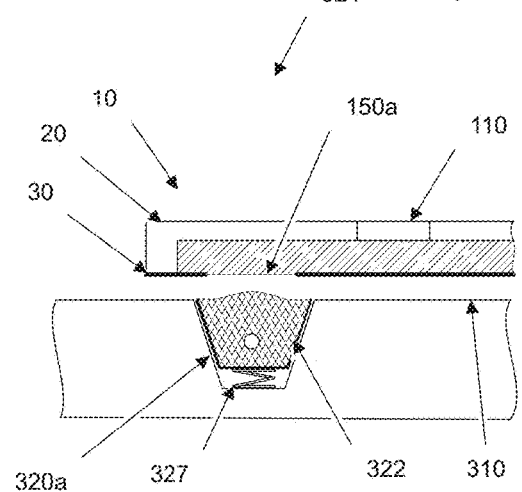
Figure 6C:
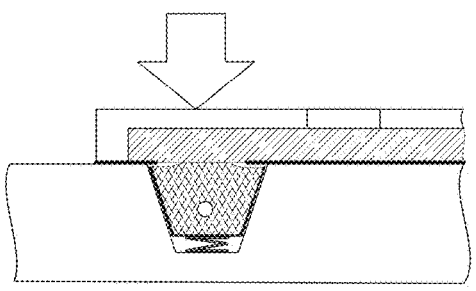

FIGS. 6b and 6c shows a schematic side view of a tray 300 and a buffer pad holder 320a with a buffer pad 322 placed therein and with an electrophoresis cassette 10 elevated slightly above the cassette support surface 310 of the tray 300 in position to be docked onto the tray 300. In order to ensure proper mating contact between the buffer pads and the buffer connection sections at the back face of the electrophoresis the mating of the buffer pads and the buffer connection sections may be biased to some degree. This may be especially important for some gel/pad compositions wherein one may get mass transfer of e.g. water from the pad into the gel, whereby the buffer pad 322 will shrink. By biasing the buffer pad 322 against the gel such situations may be accomplished for. By selecting suitable material properties for the gel component of the buffer pads 322, they may be comprised of a suitable resilient material capable of at least partially providing the biased mating. In one embodiment, the biased mating may be achieved by providing buffer strips of specific shape that allow a certain degree of compression due to its shape. In the embodiment disclosed in FIGS. 6b and 6c a spring element 327 is introduced in the buffer pad holder 320a to provide for the biased mating in combination with the material characteristics of the buffer strip and the shape of the same as is disclosed in FIG. 6c.

Figure 7:
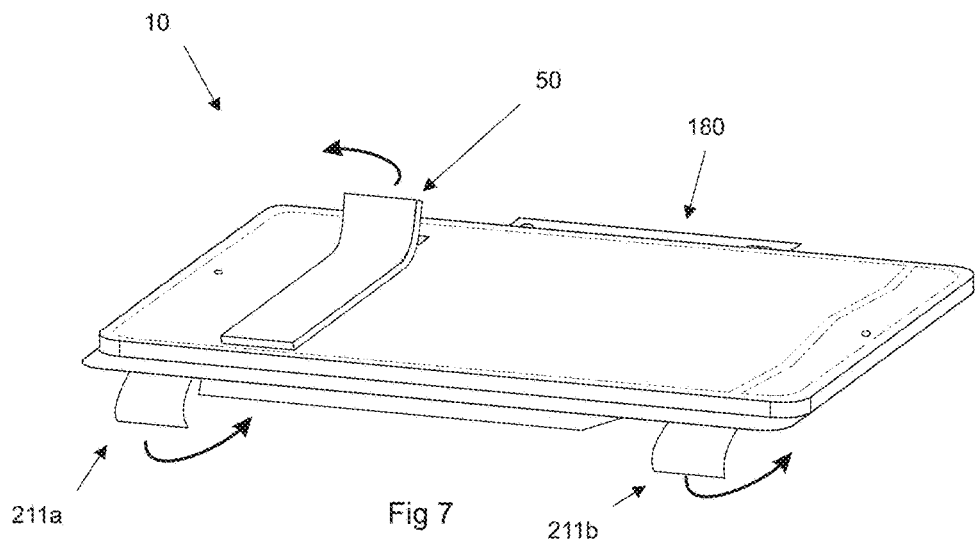
Figure 8:
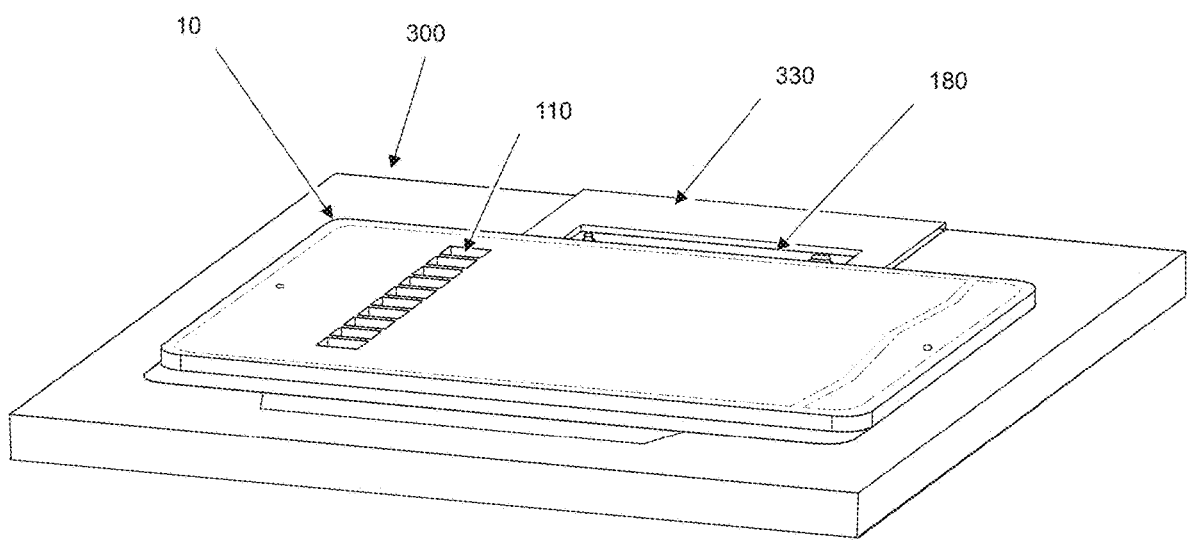
Figure 9:
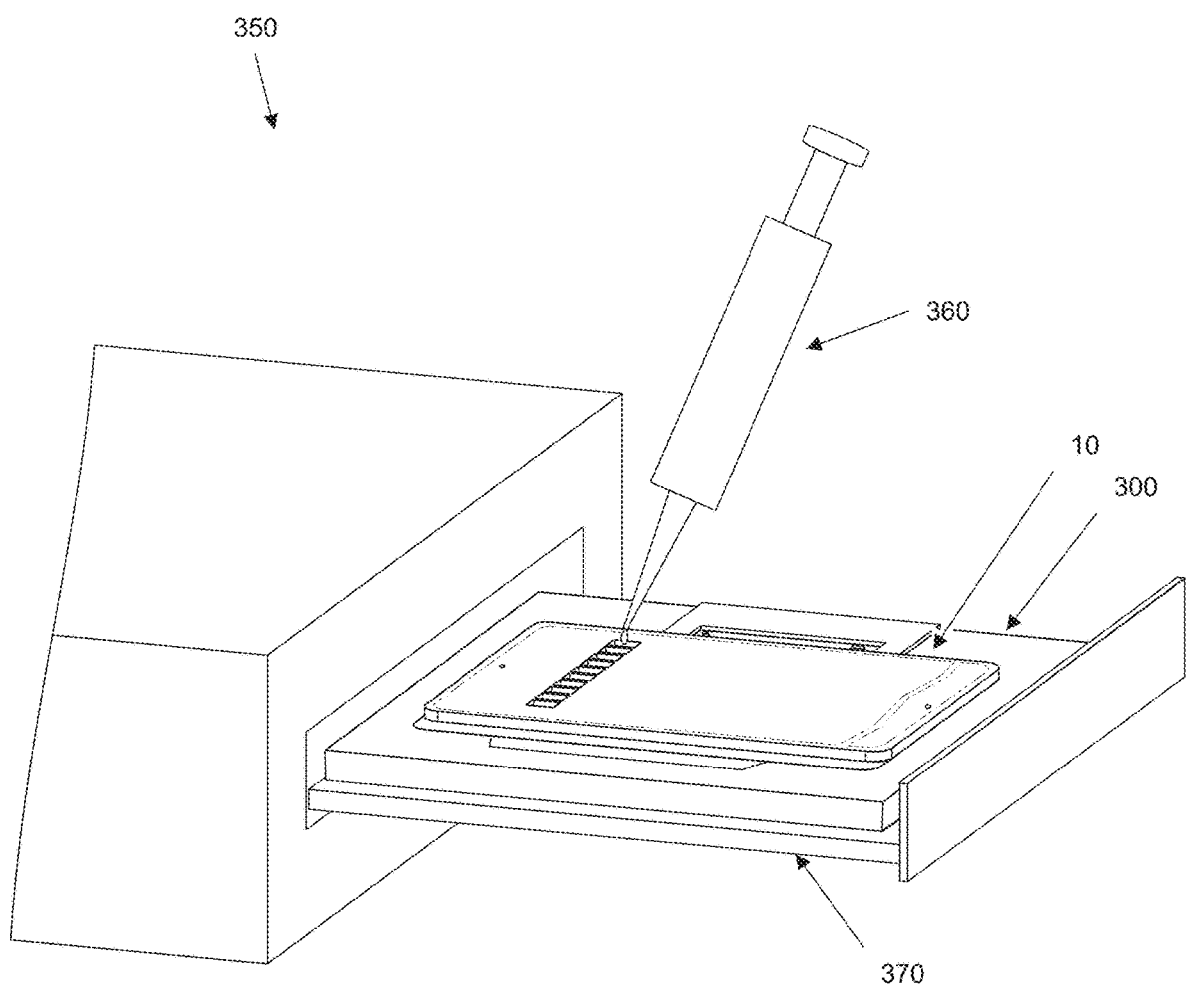

FIGS. 7 to 9 schematically show the steps involved performing an electrophoresis separation experiment using an electrophoresis cassette 10 and a compatible electrophoresis apparatus 350. The individual order of some steps may vary.

Buffer pads 322 are placed in buffer pad holders 320a and 320b in the tray 300. (FIG. 6).

Removable sections 210a and 210b of the backing film 40 are removed from the cassette 10 by pulling peal tabs 211a and 211b respectively, whereby the gel member 36 becomes exposed through the buffer slits 150a and 150b of the support frame 30 respectively. (FIG. 7)

The sample well cover 50 is removed to expose the sample wells 110 (FIG. 7)

The cassette 10 is positioned on the tray 300 with the alignment tag 180 of the support frame 30 positioned in the complementary alignment structure 330 so that proper orientation of the cassette 10 on the tray 300 is ensured. (FIG. 8)

Sample is loaded into the sample wells 110, e.g. by a pipette 360 or the like. (FIG. 9)

The electrophoresis process is performed using an electrophoresis apparatus 350. (FIG. 9)

In FIG. 9, the schematically disclosed electrophoresis apparatus 350 is provided with a tray loading mechanism 370 carrying the electrophoresis tray 300. According to one embodiment, the electrophoresis apparatus 350 comprises a fluorescence imaging unit (not shown) for imaging the result of the separation directly in the apparatus. In this way the electrophoresis cassette 10 need not to be moved to a separate imaging unit following the separation. As mentioned above, the disclosed cassette may be designed for imaging, by proper materials selection and design to avoid undesirable optical effects such as fluorescence emitted by parts of the cassette, image distortion etc. One benefit with the disclosed embodiment of the cassette 10, and electrophoresis tray 300 with buffer pads 322 recessed in the tray is that the resulting electrophoresis set up is of low profile, whereby the imaging unit may operate in the close vicinity of the gel to increase sensitivity and resolution, and to avoid negative optical effects. In the disclosed embodiment, the electrophoresis tray 300 is shown in essentially horizontal position with the gel cassette 10 arranged on top thereof. However it should be noted that the electrophoresis tray 300 as well as the gel cassette 10 may be arranged for use in other orientations such as vertical or even upside down.

In electrophoretic separation processes when pre-labeled samples are used it is often desirable to use an excess amount of label compound, e.g. Cy-dye or the like, in order to ensure an efficient labeling process of the sample to be labelled. The present inventors has observed that if only a percent or even less of the excess label, not migrates in the front of the sample constituents to be separated, the excess label discolor the separation zone where the sample constituents are present as separated "bands". Especially when running samples with a low amount of small sized sample constituents, e.g. small proteins or the like, the excess label may hide the signal from such samples in parts of the separation zone of the gel member and makes the visual impression very poor. Further, a large sample volume may escalate the problem. Still further, in case of a large sample volume, due to the extended timeframe needed to have all sample constituents migrate from the sample liquid into the gel member it has further been noted that the bands associated with the sample constituents are may be broadened. This has also been observed for post stained samples.

The present invention provides a solution to these problems by the provision of an additional step of discontinuing loading of sample constituents into the separation gel to the conventional method for electrophoretic separation at a stage when the sample constituents have been "loaded" onto the gel member and whereby excess label is prevented to be loaded onto the gel member at a later stage. It has been demonstrated that removal of the solution remaining in the well after a predetermined time, dependent on the specific separation parameters, more or less eliminates the problem with excess label in the separation-zone. Furthermore, also other disturbances like "flames", hooks and streaking that may appear as disturbances in electrophoretic separation are significantly reduced by this cleanup method. Besides enabling detection of small sized sample constituents, e.g. small proteins, in low amounts this cleanup also makes it possible to apply larger sample volumes without negative effects from the excess label, which is a common measure to take when the protein concentration of the sample is low.

The present invention may be used with essentially any type of label that may be used in association with electrophoretic separation, e.g. fluorescent labels, radioactive labels or the like, and with any type of samples that may be separated using electrophoretic separation techniques. Fluorescent labelling is accomplished using a chemically reactive derivative of a fluorophore. Common reactive groups include:

Isothiocyanate derivatives such as FITC and TRITC (derivatives of fluorescein and rhodamine) are reactive towards primary amines to form a thioureido linkage between the compound of interest and the dye.

Succinimidyl esters such as NHS-fluorescein are reactive towards amino groups to form an amido bond.

Maleimide activated fluorophores such as fluorescein-5-maleimide readily react with sulfhydryl groups. The sulfhydryl group adds to the double bond of the maleimide.

In oligonucleotide synthesis, several phosphoramidite reagents containing protected fluorescein and other fluorophores, e.g. 6-FAM phosphoramidite 2,[2] are reacted with hydroxy groups to allow the preparation of fluorophore-labelled oligonucleotides.

Reaction of any of these reactive dyes with another molecule results in a stable covalent bond formed between a fluorophore and a labelled molecule As mentioned above, pre-labeling for electrophoresis is well known (see e.g. "Electrophoresis" by Anthony T. Andrews, Clarendon Press, Oxford, 1986). And one example of a method and kit for protein labeling is provided in WO2011149415 which is incorporated herein in its entirety by reference.

Figure 10A:
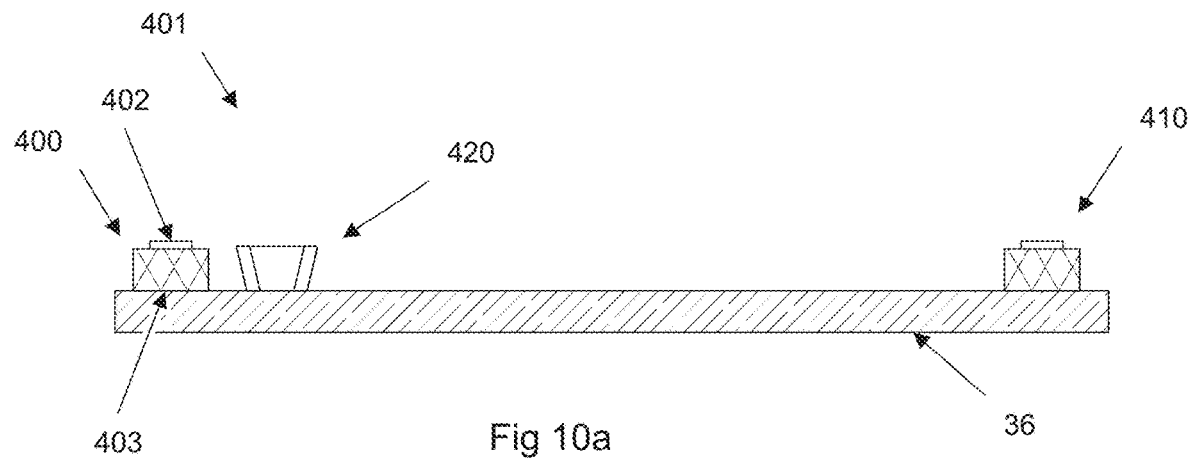
FIGS. 10 to 15 schematically show embodiments of the present invention
Figure 10B:
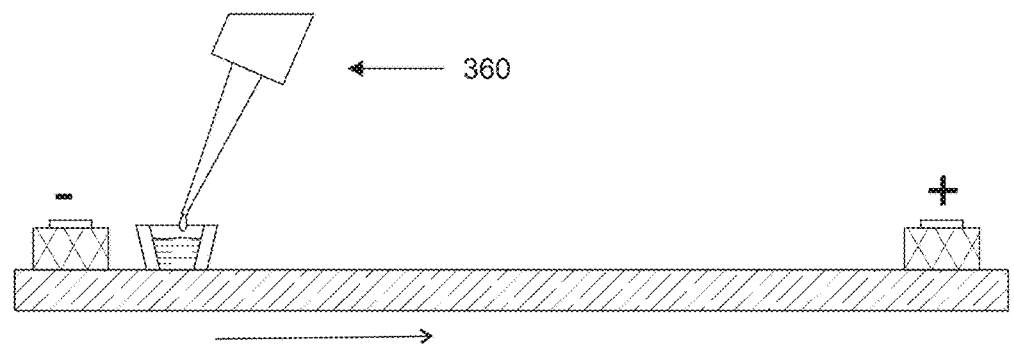
Figure 10C:
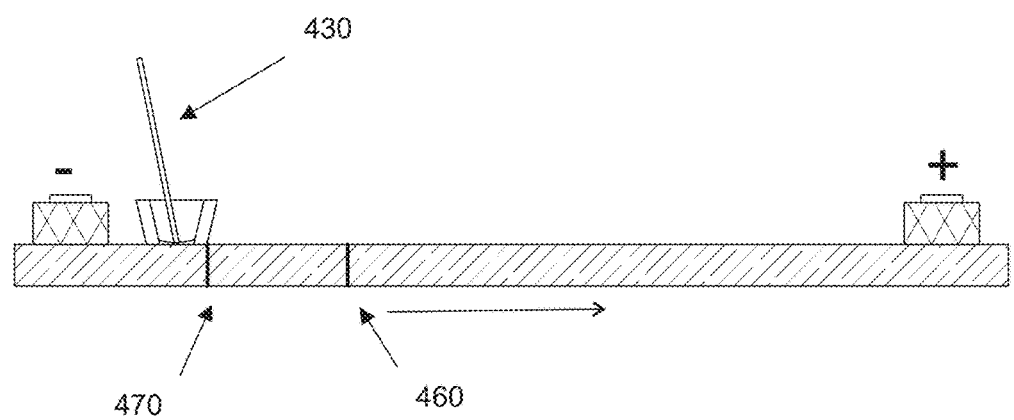

FIGS. 10a to 10c schematically discloses separation gel arrangement 401 and the steps of a method for electrophoretic separation in accordance with one embodiment of the present invention. The separation gel arrangement comprises a gel member 36 and one or more sample wells 420 for receiving sample liquid to be separated, the sample wells 420 being in fluidic contact with the gel member 36. In the disclosed embodiment, the separation gel arrangement 401 further comprises a first and a second electrode and buffer arrangement 400 and 410 respectively for applying an electric field over the gel member to drive an electrophoretic separation. In FIGS. 10a-c as well as in FIGS. 13-15, the electrode and buffer arrangements 400 and 410 are highly schematic, each comprising an electrode 402 and a bufferpad 403, and should not be considered limiting for the present invention. As mentioned above, during the separation process, the electrodes are connected to a suitable source of electric power for providing an electrical field there between. In the figures, the applied electrical power is simply indicated by + and − signs, and it should be noted that the polarity may be changed in accordance with the type of gel and sample to be separated. The bufferpads 403 may be of any suitable type as discussed above, and they are shown positioned on top of the gel member, but they may be positioned in any suitable position such as at the end surfaces at the bottom face or any combination thereof. Still further, one r more of the bufferpads may be replaced by a liquid buffer contained in a buffer container, an absorptive material or the like. In the disclosed embodiment, the sample well 420 is schematically disclosed as a cup shaped feature placed on top of the gel member 36, but it may be provided in any suitable way e.g. as is disclosed with reference to FIGS. 1 to 9, as a recess in the gel member or the like.

According to one embodiment the method for electrophoretic separation comprises the steps:

adding a sample liquid to be separated in one or more of the sample wells (FIG. 10b), applying an electric field over the gel member to drive an electrophoretic separation process, whereby sample constituents are drawn from the sample liquid in the sample well(s) into the gel member for separation, and (FIG. 10b-c)

the separation of the sample constituents indicated schematically by separation front 460 and tail 470 when a removal criteria is met: discontinuing loading of sample constituents into the separation gel (FIG. 10c) the discontinuation of loading is schematically indicated by removal of the remaining sample liquid by a sample liquid removal device 430.

Figure 11:
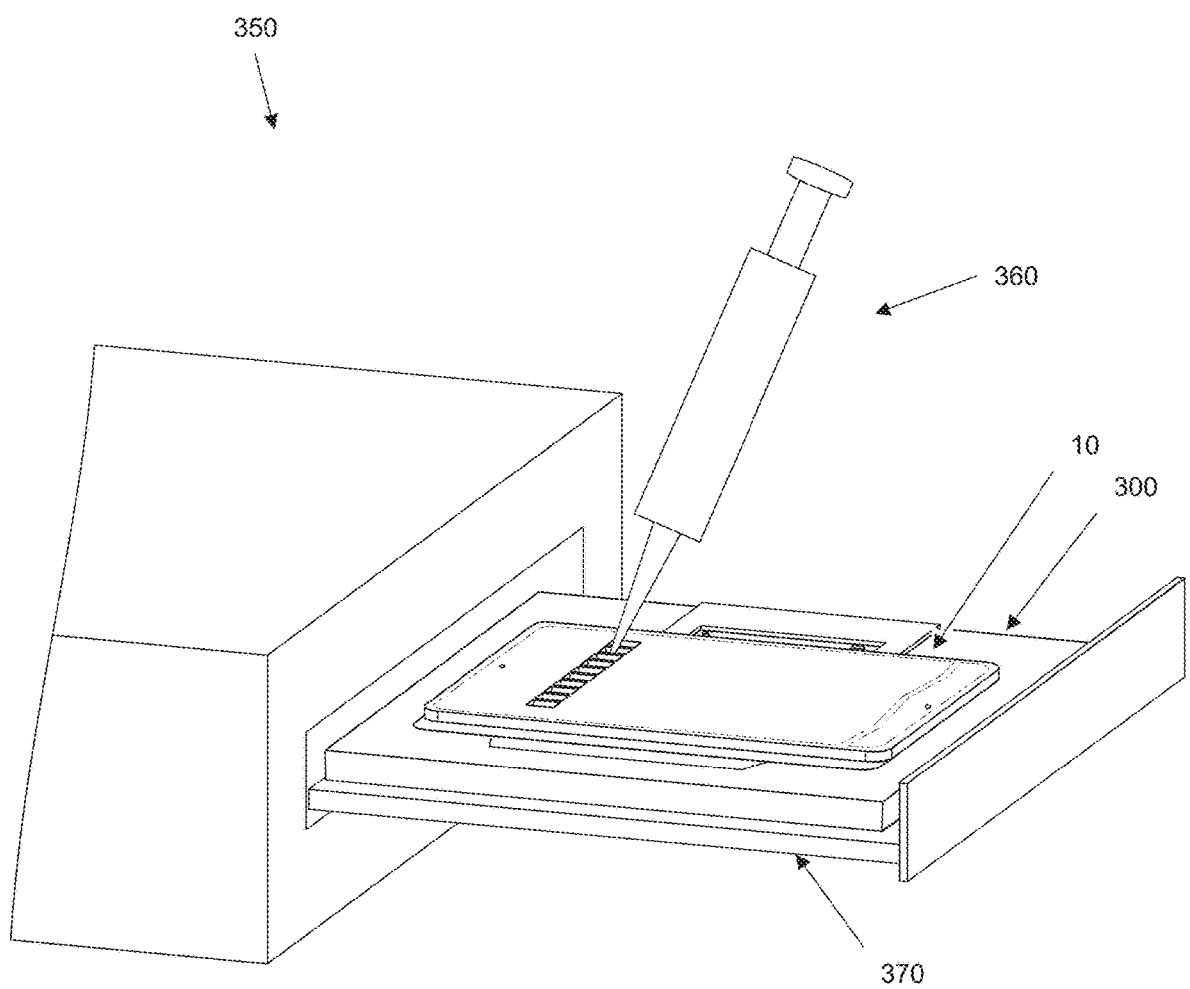

As disclosed in FIG. 10c, the discontinuation of loading of sample constituents may be achieved by removing remaining sample liquid from the one or more sample wells, but it may be performed in any suitable way that sufficiently restrict sample constituents and/or e.g. excess label to be loaded onto the gel member 36. Removal of the remaining sample liquid involves aspirating the remaining sample liquid may be performed by a sample aspiration arrangement as is disclosed in FIGS. 10c, 11, 12a and 12b. In the embodiment disclosed in FIG. 11 the aspiration arrangement is disclosed as a pipette type device 360 used to aspirate remaining sample liquid from each sample well, In more advanced embodiments, the pipette may be of multi tip type, capable of aspirating liquid from two or more sample wells in parallel, and preferably from all 10 wells simultaneously.

Figure 12A:
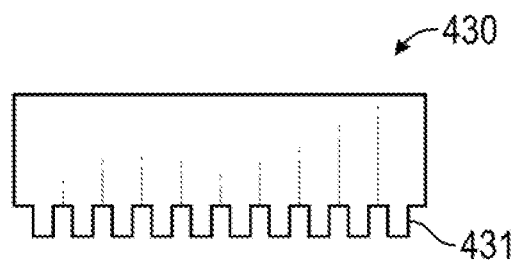
Figure 12B:
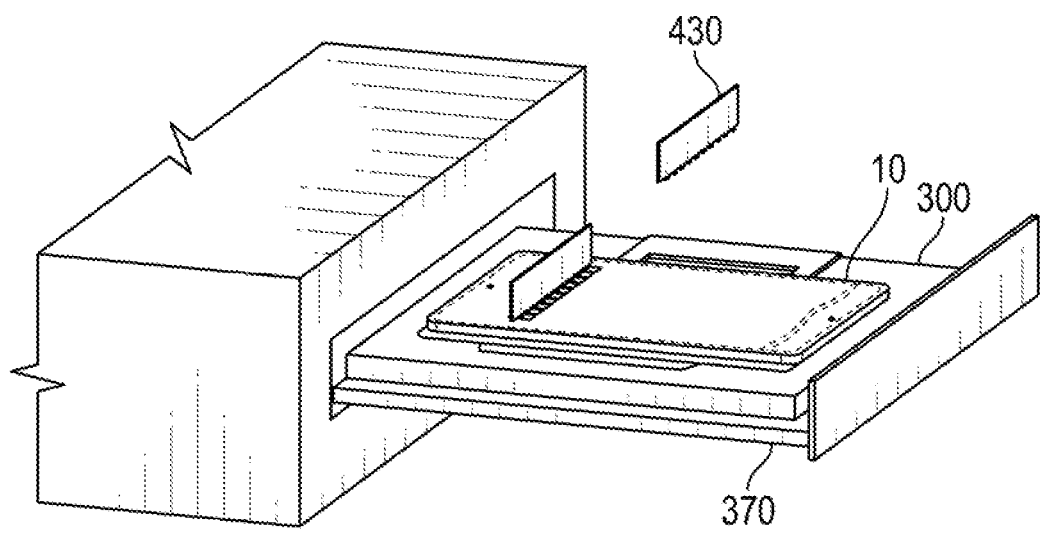

In the embodiment disclosed in FIGS. 12a and 12b the aspiration arrangement is disclosed as a sample liquid removal device 430 comprising one or more aspiration tabs 431 for aspirating remaining sample liquid from the one or more sample wells of an electrophoresis gel arrangement. According to one embodiment, the aspiration tabs 431 are comprised of an absorbing material, but in alternative embodiments, they may be of capillary type or the like. In one embodiment, the sample liquid removal device 430 is comprised of a sheet of absorbing material with aspiration tabs 431 formed therein. With respect to an electrophoresis cassette with multiple sample wells, e.g as the type disclosed in FIG. 12b, the sample liquid removal device 430 is suitably provided with aspiration tabs 431 in a matching arrangement to the wells of the cassette 10. In one embodiment a sheet of e.g. filter paper, is cut in the shape of a comb fitting into the wells of the cassette 10.

Figure 13:
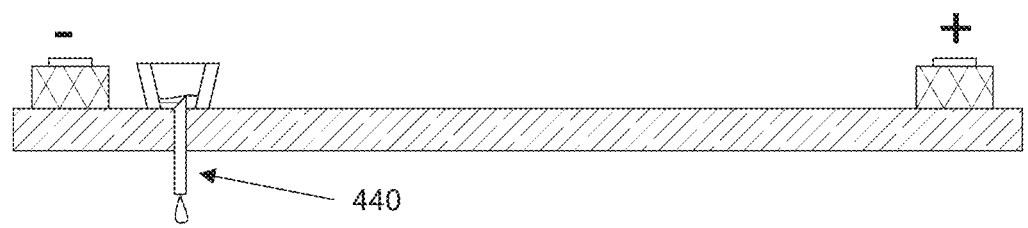

Alternatively the step of removing remaining sample liquid may be performed by draining remaining sample liquid through a sample draining arrangement 440, e.g. in the form of a syringe tip, as is shown in FIG. 13.

Figure 14A:
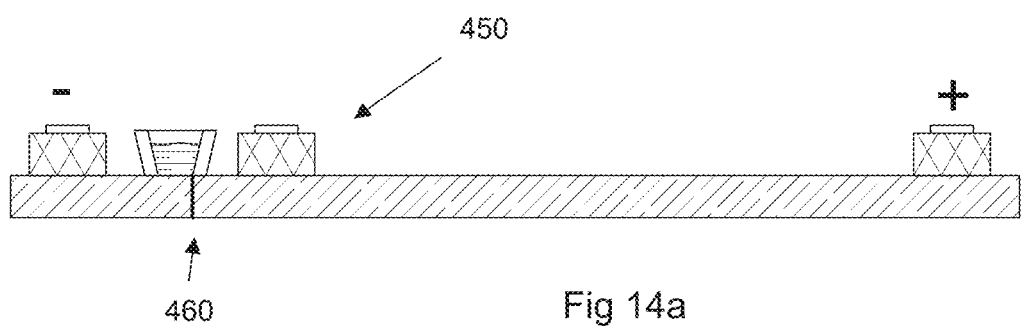
Figure 14B:
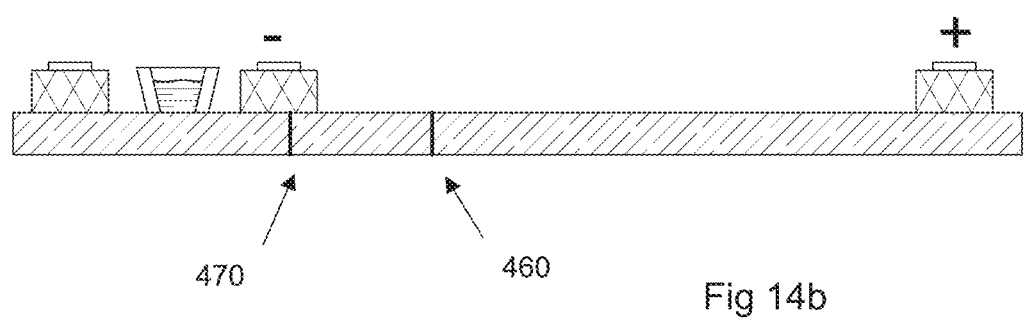

According to one embodiment schematically disclosed in FIGS. 14a and 14b, the step of discontinuing loading of sample constituents involves excluding the sample well(s) from the electric field by shifting the position of electrical contact when the separation tail 470 has been loaded onto the gel member. As tis disclosed, this may be achieved by providing an additional electrode and buffer arrangement 450 positioned downstream from the sample well with respect to the separation direction and switching on the additional electrode arrangement 450 when all relevant constituents of the sample has passed beyond the additional electrode 450. Hence, the following separation is performed based on the electric field between the additional electrode 450 and the second electrode 410 and no more sample constituents are loaded from the sample well.

Figure 15A:
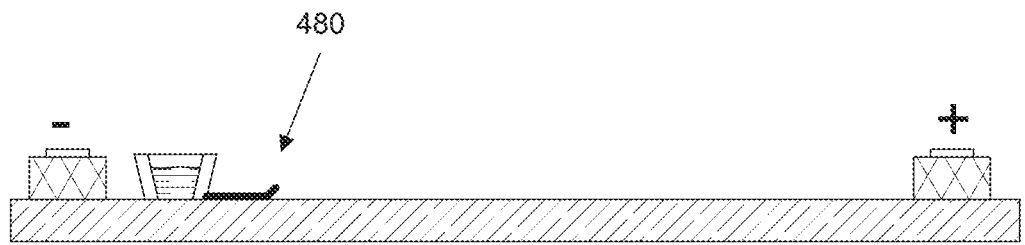
Figure 15B:

According to one embodiment schematically disclosed in FIGS. 15a and 15b, the step of discontinuing loading of sample constituents involves mechanically disconnecting the sample well(s) by a sample shutter.

According to one embodiment, the removal criteria is selected as a predetermined separation time. The predetermined time selected depends greatly on a range of parameters of the specific electrophoresis setup used, the electric power, the sample, temperature etc. For a cassette based system as disclosed in FIGS. 1 to 9, it has been determined that the separation time before discontinuing loading of sample constituents may be in the range of one minute to several tens of minutes, e.g. 2, 3, 4, 5, 6, 7, 8, 9, 10 or more minutes.

According to one embodiment, the method of the present invention the method comprises the step of monitoring the progress of the sample loading into the gel member by optical detection of the labelled sample and the removal criteria is determined based on the optical detection. In this embodiment, the removal criteria may be determined as a predefined loading ratio as optically detected.

According to one embodiment, the loading ratio is determined by the steps:
measuring the total label intensity in the sample well at start of the electrophoretic separation process,
registering the label intensity in the sample well during the electrophoretic separation process, or registering the label intensity from the sample constituents drawn from the sample liquid in the sample well(s) into the gel member during the electrophoretic separation process, and
calculating the loading ratio from the above intensities.

According to another embodiment, the removal criteria is determined based on optically detection of the position of the labelled sample, e.g. the separation front 460 and tail 470, whereby the step of discontinuing loading of sample constituents e.g. may be initiated when the separation front 460 has reached a predetermined position or the like.

Depending on the system use for running the electrophoresis separation, the electric field may be discontinued during the step of discontinuing loading of sample.

According to one embodiment, there is provided an automated electrophoresis system running the electrophoresis separation in accordance with the present invention and the system is arranged to discontinue loading of sample constituents into the separation gel when a removal criteria is met. In order to provide this, the system may be arranged to pause the electrophoresis process and prompt a user to remove remaining sample from sample wells.

The electrophoresis was paused after 5 minutes and the comb was positioned into the wells for around 5 seconds, then the comb was removed and the electrophoresis restarted. This procedure completely removes the problem with Cy-dye background in the lower third of the gel without reduction of the protein signal.

Figure 16:
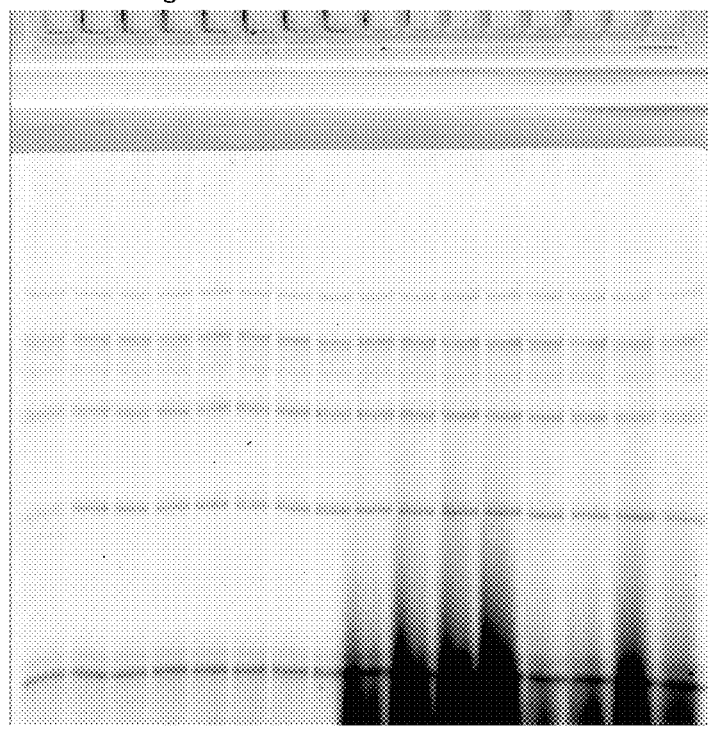
FIGS. 16 and 17 show experimental results.

FIG. 16 discloses a n image of an electrophoresis gel member after separation of samples from 16 sample wells (whereby the sample constituents from each sample well will be separated along a separate "lane"). In the disclosed experiment, the electric power was discontinued after 10 minutes and a sample liquid removal device was used to remove the remaining sample liquid from wells 1-8 before the electric power was turned on again and the electrophoretic separation completed. From FIG. 16 the effect of the present invention is clearly evident.

Figure 17:
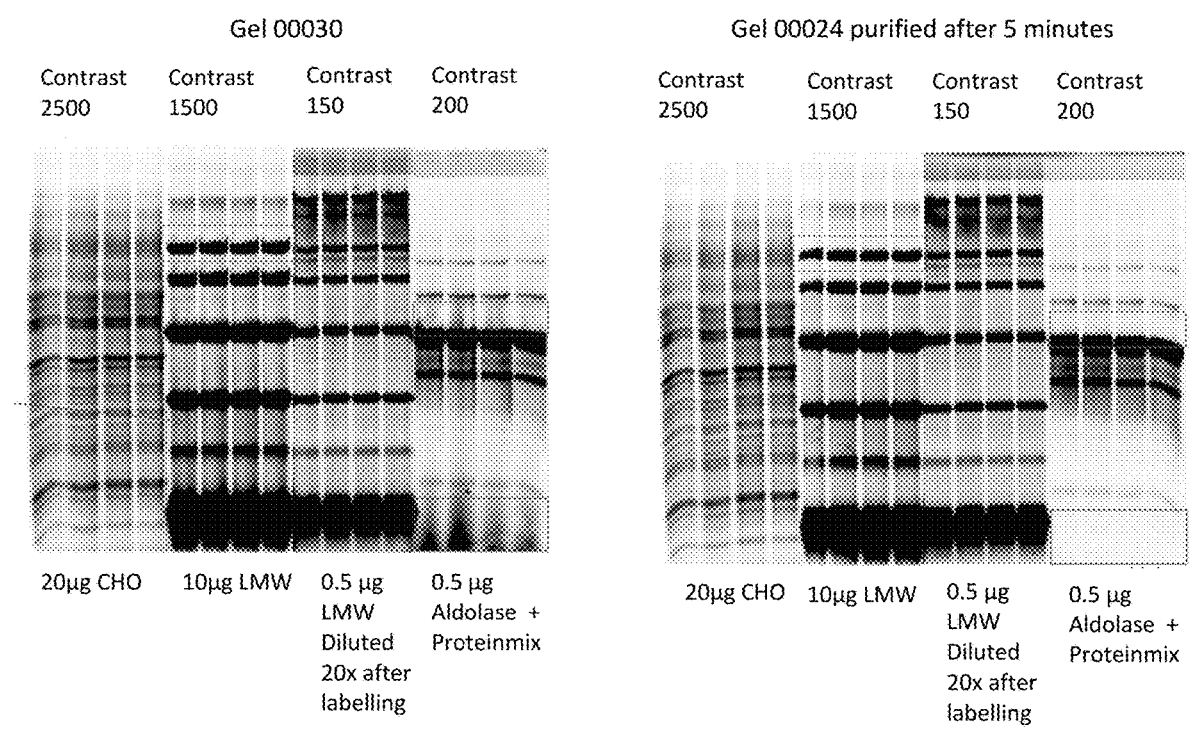

FIG. 17 shows an image montage of samples run at different Kontrats levels wherein the right hand image shows the improved results after removing the remaining sample liquid from wells after 5 minutes.

The invention claimed is:

1. A method for electrophoretic separation using a separation gel arrangement with a gel member and one or more sample wells for receiving sample liquid to be separated, the sample wells being in fluidic contact with the gel member, the method comprising the steps:
applying an electric field over the gel member to drive an electrophoretic separation process, whereby sample constituents are drawn from the sample liquid in the sample well(s) into the gel member for separation,
when a removal criteria is met: discontinuing loading of sample constituents into the separation gel,
wherein the sample comprises at least one label whereby at least one of the sample constituents is pre-labelled; and
comprising an intermediate step of monitoring the progress of the sample loading by optical detection of the labelled sample and the removal criteria is determined based on the optical detection.

2. The method according to claim 1 wherein the step of discontinuing loading of sample constituents involves removing remaining sample liquid from the one or more sample wells.

3. The method according to claim 2 wherein the step of removing remaining sample liquid involves aspirating the remaining sample liquid by a sample aspiration arrangement.

4. The method according to claim 2 wherein the step of removing remaining sample liquid involves draining remaining sample liquid through a sample draining arrangement.

5. The method according to claim 1 wherein the step of discontinuing loading of sample constituents involves excluding the sample well(s) from the electric field by shifting the position of electrical contact.

6. The method according to claim 1 wherein the step of discontinuing loading of sample constituents involves mechanically disconnecting the sample well(s) by a sample shutter.

7. The method according to claim 6 wherein removal criteria is selected as a predetermined separation time.

8. The method according to claim 7 wherein the time defined by one or more of, sample type, separation gel type, applied electric field.

9. The method according to claim 1 wherein the label is a fluorescent label or a radioactive label.

10. The method according to claim 1 wherein the removal criteria is determined as a predefined loading ratio as optically detected.

11. The method according to claim 10 wherein the loading ratio is determined by the steps:
measuring the total label intensity in the sample well at start of the electrophoretic separation process, registering the label intensity in the sample well during the electrophoretic separation process, or registering the label intensity from the sample constituents drawn from the sample liquid in the sample well(s) into the gel member during the electrophoretic separation process, and calculating the loading ratio from the above intensities.

12. The method according to claim 1 wherein the electric field is discontinued during the step of discontinuing loading of sample.

13. An automated electrophoresis system arranged to discontinue loading of sample constituents into the separation gel when a removal criteria is met in accordance with the method of claim 1.

14. An automated electrophoresis system according to claim 13 arranged to pause the electrophoresis process and prompt a user to remove remaining sample from sample wells.

15. The method of claim 3 wherein the aspiration arrangement comprises one or more aspiration tabs for aspirating the remaining sample liquid from the one or more sample wells of the electrophoresis gel arrangement.

16. The method according to claim 15 wherein the aspiration tabs are comprised of an absorbing material.

17. The method according to claim 16 wherein the aspiration arrangement is comprised of a sheet of absorbing material with the aspiration tabs formed therein.

* * * * *